United States Patent [19]

Kaminsky et al.

[11] 4,305,837

[45] Dec. 15, 1981

[54] STABILIZED AQUEOUS ENZYME COMPOSITION

[75] Inventors: George J. Kaminsky; Ronald S. Christy, both of Cincinnati, Ohio

[73] Assignee: The Procter & Gamble Company, Cincinnati, Ohio

[21] Appl. No.: 201,887

[22] Filed: Oct. 30, 1980

[51] Int. Cl.³ .................... C11D 7/42; C11D 3/386
[52] U.S. Cl. .................... 252/174.12; 252/DIG. 12; 252/114; 252/122; 252/132; 252/153; 252/527; 252/546; 252/539; 424/94
[58] Field of Search ............... 252/174.12, DIG. 12, 252/114, 122, 132, 153, 527, 546, 539; 424/94

[56] References Cited

U.S. PATENT DOCUMENTS

| | | |
|---|---|---|
| 3,325,364 | 6/1967 | Merritt et al. |
| 3,557,002 | 1/1971 | McCarty |
| 3,676,374 | 7/1972 | Zaki et al. |
| 3,893,955 | 7/1975 | Hewitt et al. |
| 4,111,855 | 9/1978 | Barrat et al. .......... 252/DIG. 12 |
| 4,243,546 | 1/1981 | Shaer ..................... 252/174.12 |

Primary Examiner—Mayer Weinblatt
Attorney, Agent, or Firm—Robert B. Aylor; Thomas H. O'Flaherty; Richard C. Witte

[57] ABSTRACT

Stabilized aqueous enzyme compositions contain a stabilizing system comprising calcium ions and a low molecular weight carboxylic acid or salt, preferably a formate, preferably with a low molecular weight alcohol, and in a pH range of from about 6.5 to about 10. Most preferred is a detergent composition containing the stabilized enzymes.

10 Claims, No Drawings

STABILIZED AQUEOUS ENZYME COMPOSITION

TECHNICAL FIELD

1. Field of the Invention

The present invention relates to stabilized aqueous enzyme compositions which preferably contain detergent compounds.

2. Description of the Art

The formulation of enzyme-containing aqueous liquid detergent compositions is very difficult due to the rapid decrease in enzymatic activity in aqueous media during storage. U.S. Pat. No. 4,111,855, Barrat et al, for Liquid Enzyme Containing Detergent Composition, issued September 5, 1978, discloses one solution to stabilization of enzymes in aqueous media. The patent utilizes a combination of a polyacid, free calcium ions, and a lower aliphatic alcohol to stabilize the enzymes.

DISCLOSURE OF THE INVENTION

The stabilized aqueous enzyme compositions of this invention comprise: (a) from 0% to about 75% of a detergent surfactant; (b) from about 0.025% to about 10%, preferably less than about 1%, of pure enzyme, preferably a proteolytic enzyme; (c) from 0% to about 60%, preferably less than about 20%, preferably from about 5% to about 15% of a low molecular weight primary or secondary alcohol; (d) from about 0.1% to about 10%, preferably from about 0.3% to about 1% for lower pH products and from about 5% to about 10% for higher pH products, of a short chain length carboxylic acid salt, preferably a formate; (e) a soluble calcium salt to give from about 0.1 to about 10, preferably from about 0.5 to about 1.5 for lower pH products and from about 4 to about 8 for higher pH products, millimoles of calcium ion per liter; and (f) the balance water, the pH of the product being from about 6.5 to about 10, preferably from about 7 to about 8.5 for enzyme stability and from about 8.5 to about 10 for detergency.

DETAILED DESCRIPTION OF THE INVENTION

Detergent Surfactants

The detergent surfactant can be selected from nonionic, anionic, cationic, zwitterionic, amphoteric and semi-polar nonionic surfactants and mixtures thereof. Preferably, the surfactant comprises a substantial portion of nonionic surfactant together with either an anionic surfactant, a semi-polar nonionic surfactant, or cationic surfactant or mixtures thereof. The surfactants are preferably from about 10% to about 75%, more preferably from about 20% to about 50% of the formula.

Nonionic Surfactants

The nonionic surfactants are conventionally produced by condensing ethylene oxide with a hydrocarbon having a reactive hydrogen atom, e.g., a hydroxyl, carboxyl, amino, or amido group, in the presence of an acidic or basic catalyst. Nonionic surfactants have the general formula $RA(CH_2CH_2O)_nH$ wherein R represents the hydrophobic moiety, A represents the group carrying the reactive hydrogen atom and n represents the average number of ethylene oxide moieties. R typically contains from about 8 to about 22 carbon atoms, but can also be formed by the condensation of propylene oxide with a lower molecular weight compound. n usually varies from about 2 to about 24.

The hydrophobic moiety of the nonionic compound is preferably a primary or secondary, straight or slightly branched, aliphatic alcohol having from about 8 to about 24, preferably from about 12 to about 20 carbon atoms. A more complete disclosure of suitable nonionic surfactants can be found in U.S. Pat. No. 4,111,855 disclosed hereinbefore and incorporated herein by reference.

Anionic Surfactants

Synthetic anionic surfactants can be represented by the general formula $R^1SO^3M$ wherein $R^1$ represents a hydrocarbon group selected from the group consisting of straight or branched alkyl radical containing from about 8 to about 24 carbon atoms and alkyl phenyl radicals containing from about 9 to about 15 carbon atoms in the alkyl group. M is a salt forming cation which typically is selected from the group consisting of sodium, potassium, ammonium, monoalkanolammonium, dialkanolammonium, trialkanolammonium, and magnesium cations and mixtures thereof.

A preferred synthetic anionic surfactant is a water-soluble salt of an alkylbenzene sulfonic acid containing from about 9 to about 15 carbon atoms in the alkyl group. Another preferred synthetic anionic surfactant is a water-soluble salt of an alkyl polyethoxylate ether sulfate wherein the alkyl group contains from about 8 to about 24, preferably from about 10 to about 18 carbon atoms and there are from about 1 to about 20, preferably from about 1 to about 12 ethoxy groups. Other suitable anionic surfactants are disclosed in U.S. Pat. No. 4,170,565, Flesher et al, issued Oct. 9, 1979, incorporated herein by reference.

Other suitable anionic surfactants can include soaps and fatty acids containing from about 8 to about 24 carbon atoms, but it should be recognized that such soaps and fatty acids do tend to tie up calcium ions and thus are preferably limited to from about 1% to about 25%, most preferably from about 10% to about 20%.

Cationic Surfactants

Suitable cationic surfactants have the general formula $R_m{}^2R_x{}^3Y_LZ$ wherein each $R^2$ is an organic group containing a straight or branched alkyl or alkenyl group optionally substituted with up to three phenyl or hydroxy groups and optionally interrupted by up to four structures selected from the group consisting of

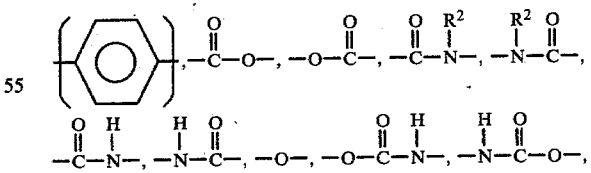

and mixtures thereof, each $R^2$ containing from about 8 to 22 carbon atoms, and which may additionally contain up to about 12 ethylene oxide groups, m is a number from 1 to 3, each $R^3$ is an alkyl or hydroxyalkyl group containing from 1 to 4 carbon atoms or a benzyl group with no more than one $R^3$ in a molecule being benzyl, x is a number from 0 to 11, the remainder of any carbon atom positions being filled by hydrogens, Y is selected from the group consisting of:

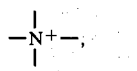 (1)

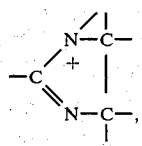 (2)

 (3)

 (4)

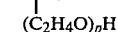 (5)

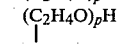 (6)

 (7)

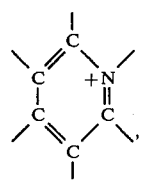 (8)

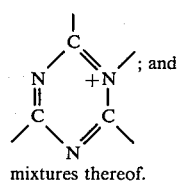 (9)

mixtures thereof.

A more complete disclosure can be found in U.S. Pat. No. 4,228,044 by Cushman M. Cambre for Laundry Detergent Composition Having Enhanced Particulate Soil Removal and Anti-redeposition Performance, issued Oct. 14, 1980, said patent being incorporated herein by reference. Care should be taken in including cationic materials, including surfactants since some cationic materials have been found to decrease enzyme effectiveness.

Zwitterionic Surfactants

Zwitterionic surfactants include derivatives of aliphatic quaternary ammonium, phosphonium, and sulphonium compounds in which the aliphatic moiety can be straight or branched chain and wherein one of the aliphatic substituents contains from about 8 to 24 carbon atoms and one contains an anionic water-solubilizing group. Particularly preferred zwitterionic materials are the ethoxylated ammonium sulfonates and sulfates disclosed in U.S. Pat. Nos. 3,925,262, Laughlin et al, issued Dec. 9, 1975 and 3,929,678, Laughlin et al, issued Dec. 30, 1975, said patents being incorporated herein by reference.

Ampholytic Surfactants

Ampholytic surfactants include derivatives of aliphatic heterocyclic secondary and ternary amines in which the aliphatic moiety can be straight chain or branched and wherein one of the aliphatic substituents contains from about 8 to about 24 carbon atoms and at least one aliphatic substituent contains an anionic water-solublizing group.

Semi-Polar Nonionic Surfactants

Semi-polar nonionic surfactants include water-soluble amine oxides containing 1 alkyl or hydroxy alkyl moiety of from about 8 to about 28 carbon atoms and 2 moieties selected from the group consisting of alkyl groups and hydroxy alkyl groups, containing from 1 to about 3 carbon atoms which can optionally be joined into ring structures; water-soluble phosphine oxides containing 1 alkyl or hydroxy alkyl moiety of from about 8 to about 28 and 2 moieties selected from the group consisting of alkyl groups and hydroxy alkyl groups, containing from about 1 to about 3 carbon atoms; and water-soluble sulfoxides containing 1 alkyl or hydroxy alkyl moiety of from about 8 to about 28 carbon atoms and a moiety selected from the group consisting of alkyl and hydroxy alkyl moieties of from 1 to 3 carbon atoms.

For a more complete disclosure of compounds which are suitable for incorporation in detergent compositions, one can consult U.S. Pat. Nos. 4,056,481, Tate (Nov. 1, 1977); 4,049,586, Collier (Sept. 20, 1977); 4,040,988, Vincent et al (Aug. 9, 1977); 4,035,257, Cherney (July 12, 1977); 4,033,718, Holcolm et al (July 5, 1977); 4,019,999, Ohren et al (Apr. 26, 1977); 4,019,998, Vincent et al (Apr. 26, 1977); and 3,985,669, Krummel et al (Oct. 12, 1976); all of said patents being incorporated herein by reference.

THE ENZYMES

The enzyme component herein is incorporated in an amount of from about 0.025 to about 1%, preferably from about 0.05% to about 0.2%. The preferred proteolytic enzyme component should give to the composition a proteolytic activity of at least about 4 Anson units per liter, preferably from about 15 to about 70 Anson units per liter, most preferably from about 20 to about 40 Anson units per liter. A proteolytic activity of from about 3 to about 5 Anson units per gram of product is desirable. Other enzymes, including amylolytic enzymes can also be included.

Preferably the enzyme component is characterized by an isoelectric point of from about 8.5 to about 10, preferably from about 9 to about 9.5.

Examples of suitable proteolytic enzymes include many species which are known to be adapted for use in detergent compositions and, in fact, have been used in detergent compositions. Sources of the enzymes include commercial enzyme preparations such as "Alcalase" sold by Novo Industries, and "Maxatase" sold by Gist-Brocades, Delft, The Netherlands, which contain from about 10% to about 20% enzyme. Other preferred enzyme compositions include those commercially available under the tradenames SP-72 ("Esperase") manufactured and sold by Novo Industries, A/S, Copenhagen, Denmark and "AZ-Protease" manufactured and sold by Gist-Brocades, Delft, The Netherlands.

A more complete disclosure of suitable enzymes can be found in U.S. Pat. No. 4,101,457, Place et al issued July 18, 1978, incorporated herein by reference.

The Alcohol

The low molecular weight primary or secondary alcohol is exemplified by methanol, ethanol, propanol, and isopropanol. Monohydric alcohols are preferred for solubilizing the surfactant but polyols containing from 2 to about 6 carbon atoms and from 2 to about 6 hydroxy groups can be used and can provide improved enzyme stability. Examples of polyols include propylene glycol, ethylene glycol and glycerine. Ethanol is a particular preferred alcohol. The composition contains from 0% to about 20%, preferably from about 5% to about 15%, most preferably from about 9% to about 11.4% of the alcohol.

The Carboxylic Acid Salt

The short chain carboxylic acid salt is preferably water-soluble and more preferably is a formate, e.g., sodium formate. The formates are surprisingly much more effective than other short chain carboxylic salts like the acetates and the propionates. The short chain carboxylic acid salt is used at a level from about 0.1% to about 10%, preferably from about 0.3% to about 3%, more preferably from about 0.5% to about 1.5% when the product pH is below about 8.5 and from about 3% to about 10%, preferably from about 4% to about 8%, when the product pH is from about 8.5 to about 10. At the higher pH's (8.5–10) only formates are suitable.

The Calcium-Ions

Any water-soluble calcium salt can be used as a source of calcium ions, including calcium acetate, calcium formate and calcium propionate. The level of calcium ions in the composition is from about 0.1 to about 10 millimoles of calcium ion per liter, preferably from about 0.5 to about 1.5 millimoles of calcium ion per liter when the product pH is below about 8.5 and from about 4 to about 8 millimoles when the product pH is from about 8.5 to about 10. When soap or fatty acid is present, the preferred level is from about 2 to about 6 millimoles of calcium ion per liter. Zinc and magnesium ions can replace the calcium ion completly or in part.

Product pH

The pH of the product is from about 6.5 to about 10, preferably from about 7 to about 8.5 to obtain a combination of enzyme stability and detergency. A pH of from about 8.5 to about 10 preferably 9 to 10 is best for detergency. Both high and low pH's adversely affect enzyme stability and low pH's give up too much detergent effectiveness. Suitable pH buffers include mono-, di- and tri-ethanolamines. When the product pH is from 8.5 to about 10 triethanolamine is the best buffer. When soap or fatty acid is present, the preferred pH is from about 7 to about 7.5.

The balance of the composition is usually water, but the composition can contain other ingredients, including perfumes, dyes, opacifiers, optical brighteners, suds suppressors, pH adjusting agents, etc. Disclosures of suitable ingredients can be found in the patents and patent applications incorporated herein by reference. Preferably, the product is essentially free of materials such as detergent builders that tie up calcium ions to permit sufficient free calcium ions to be present although with the formate, excellent stability is achieved with very low levels of calcium ions, especially in the low pH range.

Preferred Compositions Containing Soap (low pH range only)

In a preferred embodiment homogeneous aqueous detergent compositions of this invention comprise: (a) from about 20% to about 50% by weight of an organic synthetic surface-active agent; (b) from about 3% to about 15% by weight of a saturated fatty acid having 10 to 16 carbon atoms in the alkyl chain; (c) from 0.025% to about 1% by weight of an enzyme; (d) from 0.1% to about 3% by weight of a carboxylic acid having from 1 to 3 carbon atoms; and (e) less than 2 millimoles of enzyme-accessible calcium per kilo of the detergent composition, the pH of the composition measured as is at 20° C., being from about 6.5 to 8.5. In these preferred embodiments of this invention, the saturated fatty acids preferably have from 12 to 14 carbon atoms in the alkyl chain, the detergent enzymes are represented by proteases or mixtures of proteases and amylases, the short chain carboxylic acid is represented by formic acid, the enzyme-accessible calcium is present in an amount of from about 0.5 to 1.5 millimoles per kilo of the detergent composition, and the pH of the composition, as is, is in the range from about 7 to about 7.5. These preferred compositions of this invention are substantially builder free. While the fatty acids and/or soaps are not considered as detergent builders/sequestrants in the context of this invention, the claimed compositions do not contain more than minor amounts of sequestrants.

The Saturated Fatty Acid

In this preferred embodiment, the saturated fatty acid component is incorporated in an amount of from about 3% to about 15%, preferably from about 5% to about 11%. The saturated fatty acids have from 10 to 16, preferably 12 or 14 carbon atoms in the alkyl chain. The most preferred fatty acids are either lauric acid or lauric and myristic fatty acid in a mixture of 5:1 to 1:1. It is understood that in addition to the saturated fatty acids, the compositions herein can comprise certain amounts of unsaturated fatty acids having, for example, 16 or 18 carbon atoms in the alkyl chain. Known examples of the like unsaturated fatty acids are olefic fatty acid and palmitoleic fatty acid.

The Enzyme

In this preferred embodiment the enzyme component is incorporated in an amount of from about 0.025 to about 1%, preferably from about 0.5% to about 0.2%. The preferred proteolytic enzyme component should give to the composition a proteolytic activity of at least about 4 Anson units, preferably from about 8 to about 30 Anson units, most preferably from about 10 to about 20 Anson units per kilo of the liquid detergent composition. In another preferred embodiment. the enzyme component can be represented by a mixture of proteases and amylases. The proteolytic activity of that mixture is as defined hereinbefore.

Preferably the enzyme component is characterized by an isoelectric point of from about 8.0 to about 10, preferably from about 8.5 to about 9.5.

The Carboxylic Acid

In this preferred embodiment this ingredient is used in an amount from 0.1% to about 3%, preferably from 0.5% to 1.5% by weight. Preferred are the water-soluble salts. Most preferred is formic acid or the formates such as sodium, potassium, lithium, amines and substituted amines, inclusive of mono-, di-, and tri-ethanolamines.

The Enzyme-Accessible Calcium

These preferred compositions herein comprise less than about 2, preferably from 0.5 to 1.5, millimoles of enzyme-accessible calcium per kilo of the homogenous enzyme containing detergent product. The claimed compositions are substantially free of sequestrants, for example, polyacids capable of forming calcium complexes which are soluble in the composition. However, minor amounts of sequestrants such as polyacids or mixtures of polyacids can be used. The enzyme-accessible calcium is defined as the amount of calcium-ions effectively available to the enzyme component. The calcium sequestration resulting from e.g., 0.5% of a mixture of polyphosphonates and polyacids as exemplified hereinafter can represent about 1 to about 1.5 millimoles of calcium per kilo of product. The total calcium incorporated into the compositions is thus comprised of the enzyme-accessible calcium and also the calcium sequestered by the low levels of polyacids. From a practical standpoint the enzyme-accessible calcium is therefore the soluble calcium in the composition in the absence of any strong sequestrants, e.g., having an equilibrium constant of complexation with calcium equal to or greater than 1.5 at 20° C.

Product pH

The pH of these preferred products is from about 6.5 to about 8.5, preferably from about 7 to about 7.5 to obtain a combination of enzyme stability and detergency. Both high and low pH's can adversely affect enzyme stability.

Optional Components

In addition to the essential ingredients described hereinbefore the preferred compositions herein frequently contain a series of optional ingredients which are used for the known functionality in conventional levels. While the inventive compositions are premised on aqueous enzyme-containing detergent compositions containing a critical ternary system as fully explained above, it is frequently desirable to use a phase regulant. This component together with water constitutes then the solvent matrix for the claimed liquid compositions. Suitable phase regulants are well-known in liquid detergent technology and, for example, can be represented by lower aliphatic alcohols having from 2 to 6 carbon atoms and from 1 to 3 hydroxyl groups, ethers of diethylene glycol and lower aliphatic monoalcohols having from 1 to 4 carbon atoms. Specific examples of phase regulants are: ethanol; n-propanol; isopropanl; butanol; 1,2-propanediol; 1,3-propanediol; n-hexanol; mono-methyl-, -ethyl-, -propyl, and mono-butyl ethers and di-ethylene glycol. Additional phase regulants having a relatively high boiling point and low vapor pressure can also be used provided they do not react with the other ingredients of the compositions.

Known detergent hydrotropes are a further class of phase regulants suitable for use herein. Examples of these hydrotropes include salts of alkylarylsulfonates having up to 3 carbon atoms in the alkyl group, e.g., sodium, potassium, ammonium and ethanolamine salts of xylene-, toluene-, ethylbenzene-, cumene-, and isopropylbenzene sulfonic acids. The phase regulant is frequently used in an amount from about 5% to about 20%; the sum of phase regulant and water is normally in the range from 65% to 35%.

The preferred compositions herein can contain a series of further optional ingredients which are mostly used in additive levels, usually below about 5%. Examples of the like additives include: polyacids, suds regulants, opacifiers, antioxidants, bactericides, dyes, perfumes, brighteners and the like.

A preferred additive is represented by a polyacid or mixture of polyacids in an amount below about 1%. Suitable polyacids can include: citric, cyclohexane-1,1-dicarboxylic, cyclopropane-1,1-dicarboxylic, dimethylmalic, glutaric, o-hydroxybenzoic, m-hydroxybenzoic, p-hydroxybenzoic, itaconic, methylsuccinic, sodium tripolyphosphates, and nitrilotriacetic acid. Preferred polyacid species for use herein can be represented by citric acid and organo-phosphonic acids and mixtures thereof. Particularly preferred alkylene-polyaminopolyalkylene phosphonic acids are ethylene diamine tetramethylenephosphonic acid, hexamethylene diaminetetramethylene phosphonic acid, diethylene triaminepentamethylenephosphonic acid, and aminotrimethylenephosphonic acid or the salts thereof. These organophosphonic acids/salts are preferably used in an amount from 0.1%–0.8%.

The beneficial utilization of the claimed compositions under various usage conditions can require the utilization of a suds regulant. While generally all detergent suds regulants can be utilized preferred for use herein are alkylated polysiloxanes such as dimethylpolysiloxane also frequently termed silicones. The silicones are frequently used in a level not exceeding 0.5%, most preferably between 0.01% and 0.2%.

It can also be desirable to utilize opacifiers inasmuch as they contribute to create a uniform appearance of the concentrated liquid detergent compositions. Examples of suitable opacifiers include: polystyrene commercially known as LYTRON 621 manufactured by MONSANTO CHEMICAL CORPORATION. The opacifiers are frequently used in an amount from 0.3% to 1.5%.

The compositions herein can also contain known antioxidants for their known utility, frequently radical scavengers, in the art established levels i.e. 0.001% to 0.25% (by reference to total composition). These antioxidants are frequently introduced in conjunction with the fatty acids. While many suitable antioxidants are readily known and available for that purpose especially preferred for use in the compositions herein are: 2,6 ditertiary butyl-p-cresol, more commonly known as butylated hydroxytoluene, BHT, and 2-tertiarybutyl-4-hydroxyanisole or 3-tertiarybutyl-4-hydroxyanisole more commonly known as BHA or butylated hydroxyanisole. Other suitable antioxidants are: 4,4'thiobis(6-tert-butyl-m-cresol) and 2-methyl-4,6-dinonyl phenol.

The following examples illustrate the invention and facilitate its understanding.

All parts, percentages and ratios herein are by weight unless otherwise specified.

EXAMPLE I

| Base formula | |
|---|---|
| Ingredient | % of Formula |
| $C_{12-13}$ alkyl polyethoxylate (6.5) | 25 |
| Anionic Surfactant (as indicated) | 12.5 |
| Ethanol | 10 |

-continued

| Base formula | |
|---|---|
| Water | 50 |
| Monoethanolamine (LAS) or NaOH (AE₃S) | To neutralize |
| Maxazyme (Maxatase) Enzyme Slurry (0.045 Anson units/g. of product) pH 7.5 | 1 (as 50% slurry) |

| Run | Anionic | % Sodium Acetate | % Sodium Propionate | % Sodium Formate | CaCl$_2$ | % Retained Activity After 14 days at 100° F. |
|---|---|---|---|---|---|---|
| 1 | C$_{11.8}$ alkyl benzene sulfonic acid (LAS) | — | 0.5 | — | 0.011 | 50% |
| 2 | C$_{12-14}$ alkyl polyethoxylate (3) sulfuric acid (AE₃S) | 0.5 | — | — | .011 | 75.4% |
| 3 | AE₃S | 0.5 | — | — | .011 | 77.5% |
| 4 | AE₃S | 0.5 | — | — | .011 | 76.7% |
| 5 | LAS | — | — | 0.5 | .011 | 100% |
| 6 | AE₃S | — | — | 0.5 | .011 | 95.5% |
| 7 | AE₃S | — | — | 0.5 | — | 88% |

21 Day stability data follows the same general trend. As can be seen from the above data, the formate is best, followed by the acetate, which is followed by the propionate. The total amount of Ca$^{++}$ present is about 15 millimoles/liter. (Some is added with the enzyme slurry.)

EXAMPLE II

Liquid detergent compositions were prepared by mixing the individual ingredients listed hereinafter in the stated proportions.

| INGREDIENTS | COMPOSITIONS | | | | | | |
|---|---|---|---|---|---|---|---|
| | 1 | 2 | 3 | 4 | 5 | 6 | 7 |
| Linear dodecyl benzene sulfonic acid | 14 | 14 | 14 | 14 | 14 | 14 | 14 |
| Condensation product of one mole C$_{13}$-C$_{15}$ oxo-alcohol and 7 moles of ethylene oxide | 15 | 15 | 15 | 15 | — | — | — |
| Condensation product of one mole C$_{13}$-C$_{15}$ branched alcohol (50% branching) and 4 moles of ethylene oxide | — | — | — | — | 10 | 10 | 10 |
| Condensation product of one mole branched (60%) C$_{16}$-C$_{19}$ oxo-alcohol and 11 moles of ethylene oxide | — | — | — | — | 20 | 20 | 20 |
| Hardened and topped coconut fatty acid (a) | 10 | 10 | 10 | 10 | — | — | — |
| Oleic acid (85% purity) | 5 | 5 | 5 | 5 | — | — | — |
| C$_{16}$-C$_{22}$ hardened fish oil fatty acid | — | — | — | — | 0.5 | 0.5 | 0.5 |

-continued

| INGREDIENTS | COMPOSITIONS | | | | | | |
|---|---|---|---|---|---|---|---|
| | 1 | 2 | 3 | 4 | 5 | 6 | 7 |
| Sodium hydroxide | 1.75 | 1.75 | 1.75 | 1.75 | — | — | — |
| Ethanol | 10 | 10 | 10 | 10 | 10 | 10 | 10 |
| 1,2-propanediol | 4 | 4 | 4 | 4 | — | — | — |
| Triethanolamine to adjust pH to: | 7 | 7 | 7 | 7 | 7 | 7 | 7 |
| Sodium formate | 0 | 0.5 | 1.0 | 2.0 | 0 | 1.0 | 2.0 |
| Alkaline protease (b) | 0.05 | 0.05 | 0.05 | 0.05 | 0.05 | 0.05 | 0.05 |
| Diethylenetriamine pentamethylene phosphoric acid | 0.3 | 0.3 | 0.3 | 0.3 | 0.3 | 0.3 | 0.3 |
| Silicone suds regulant emulsion, perfume, opacifier, brightener, dye, anti-oxidant and water | Balance to 100 | | | | | | |

(a) C$_8$-C$_{10}$ fraction has been stripped.
(b) MAXATASE® supplied by GIST-BROCADES, expressed on 100%-active basis.

The compositions I–IV contained 3 millimoles and compositions V–VII 5 millimoles of calcium/liter of the composition.

The storage stability of the listed compositions was determined under high temperature conditions (35° C. 2 and 4 weeks; 40° C. 48 hours). It was found that compositions II, III, IV, VI and VII in accordance with this invention were markedly superior vs. comparable compositions I and V which did not contain the formate stabilizer.

Substantially comparable results are also provided by compositions III and VI wherein the sodium formate is replaced by a substantially equivalent molar level of a salt selected from: triethanolammonium formate, diethanolammonium formate; monoethanolammonium formate; potassium formate; lithium formate and ammonium formate.

EXAMPLE III

Liquid detergent compositions were prepared by mixing the listed ingredients in the stated proportions.

| INGREDIENTS | COMPOSITIONS | | | |
|---|---|---|---|---|
| | A | B | C | I |
| Linear dodecylbenzene sulfonic acid | 14 | 14 | 14 | 14 |
| Condensation product of one mole of C$_{13}$-C$_{15}$ OXO alcohol and 7 moles of ethylene oxide | 30 | 15 | 15 | 15 |
| Lauric acid | — | 10 | 10 | 10 |
| Oleic acid | — | 5 | 5 | 5 |
| Triethanolamine | 8.5 | 5 | 5 | 5 |
| Sodium hydroxide to adjust pH to: | 7 | 7 | 7 | 7 |
| Ethanol | 10 | 10 | 10 | 10 |
| 1,2 propanediol | — | 4 | 4 | 4 |
| Proteolytic enzyme (a) | 0.05 | 0.05 | 0.05 | 0.05 |
| Calcium (b) (c) | 4 | 4 | 2.0 | 2.0 |
| Sodium formate | — | — | — | 1.0 |
| Citric acid | 0.2 | 0.2 | 0.2 | 0.2 |
| Diethylenetriamine pentaphosphonic acid | 0.3 | 0.3 | 0.3 | 0.3 |
| Silicone suds regulant emulsion, brightener, perfume, opacifier, dye, antioxidant and water | BALANCE TO 100 | | | |

(a) MAXATASE® supplied by GIST-BROCADES expressed on a 100% active basis.
(b) Added as calcium chloride and expressed as millimoles of calcium ion per kilo of composition.
(c) The level of enzyme-accessible calcium is: composition A:2.5; B:2.5; C:0.5; and I:0.5.

The enzyme and physical stability of the listed compositions were determined under accelerated storage conditions after 2 weeks at 35° C. Composition A is representative of the prior art. Compositions B and C are reference compositions based on routine variations vs. the art compositions. Composition I is an example of the invention herein. The level of calcium in compositions A and B represents, based on current art knowledge, the minimum needed to achieve acceptable enzyme stability. The amount of calcium in composition C was lowered to the point where phase instability and precipitation would not anymore occur. The testing data are summarized below.

|  | COMPOSITION | | | |
| --- | --- | --- | --- | --- |
|  | A | B | C | I |
| Residual enzyme-Stability after 2 weeks at 35° C. (%) | 66 | 42 | 18 | 85 |
| Product appearance | precipitation | precipitation | clear | clear |

These results confirm the overall performance benefits provided by composition I in accordance with this invention vs. formulationwise closely related art composition —A— or what could be technical variations —B, C— of known art formulations.

Comparable performance benefits are obtained from the above compositions wherein the formic acid is replaced with an identical molar proportion of acetic acid or propionic acid. p Further compositions of this invention were prepared by mixing the listed components in the indicated proportions.

|  | COMPOSITIONS | | |
| --- | --- | --- | --- |
| INGREDIENTS | D | IV | V |
| Linear dodecylbenzene sulfonic acid | 14 | 14 | 14 |
| Condensation product of one mole of $C_{13}$-$C_{15}$ OXO alcohol with 35% of branching and 7 moles of ethylene oxide | 15 | 15 | 15 |
| Lauric acid | 10 | 10 | 10 |
| Oleic acid | 5 | 5 | 5 |
| Triethanolamine | 5 | 5 | 5 |
| Sodium hydroxide to adjust pH to: | 7 | 7 | 7 |
| Ethanol | 10 | 10 | 10 |
| 1,2 propylene glycol | 4 | 4 | 4 |
| Proteolytic enzyme (a) | 0.05 | 0.05 | 0.05 |
| Calcium (b) | 1.5 | 1.5 | 1.5 |
| Formic acid (c) | — | 0.68 | — |
| Acetic acid (c) | — | — | 0.88 |
| Citric acid | 0.2 | 0.2 | 0.3 |
| Diethanolamine pentaphosphonic acid | 0.3 | 0.3 | 0.3 |
| Silicone suds regulant emulsion, brightener, perfume, opacifier, dye, antioxidant and water | BALANCE TO 100 | | |

(a) MAXATASE ® supplied by GIST-BROCADES and expressed on a 100% active basis
(b) Total calcium added as calcium chloride and expressed in millimoles of calcium ion per liter of solution.

Composition D is what could be a technical variation of the state of art whereas formulae IV and V are executions of the claimed invention.

The residual enzymatic activity (expressed in % of initial activity) were measured following exposure to accelerated storage conditions (48 hours at 40° C.).

The testing results were as follows:

|  | Compositions | | |
| --- | --- | --- | --- |
|  | D | IV | V |
| Residual enzymatic activity (in %) | 25 | 64 | 48 |

These results verify the superiority of the claimed technology vs. closely related compositions and also show that formic acid is the most preferred short chain carboxylic acid.

A series of additional compositions of this invention are prepared by mixing the listed ingredients in a conventional manner.

|  | COMPOSITIONS | | | | | | |
| --- | --- | --- | --- | --- | --- | --- | --- |
| INGREDIENTS | VI | VII | VIII | IX | X | XI | XII |
| Linear dodecylbenzene sulfonic acid | 14 | 6 | 14 | 14 | 10 | 14 | 14 |
| Condensation product of one mole of $C_{14}$-$C_{15}$ OXO alcohol with 20% branching and 7 moles of ethylene oxide | 20 | 30 | — | — | — | 20 | — |
| Condensation product of one mole of $C_{13}$-$C_{15}$ OXO alcohol with 25% branching and 4 moles of ethylene oxide | — | — | — | 5 | — | — | — |
| Condensation product of one mole of $C_{16}$-$C_{19}$ OXO alcohol highly branched (60%) and 11 moles of ethylene oxide | — | — | — | 10 | — | — | — |
| Condensation product of one mole of $C_{13}$-$C_{15}$ OXO alcohol with 35% branching and 7 moles of ethylene oxide | — | — | 20 | — | 15 | — | 20 |
| Lauric acid | 10 | 10 | 5 | 5 | — | — | — |
| Coconut acid (hardened & stripped) (a) | — | — | — | — | 10 | 5 | 10 |
| Oleic acid | 5 | — | 8 | 8 | 5 | 10 | 5 |
| Proteolytic enzyme (b) | 0.05 | 0.05 | 0.05 | 0.05 | 0.05 | 0.05 | 0.05 |
| Calcium (c) | 1.5 | 2 | 1.6 | 2.0 | 1.5 | 0.5 | 1.0 |
| Sodium formate | 1.0 | 1.5 | 1.0 | 0.5 | 1.0 | 0.5 | 1.0 |
| Triethanolamine | 5 | 5 | 5 | 5 | 5 | 5 | 5 |
| Sodium hydroxide up to pH | 7 | 7 | 7 | 7.5 | 6.8 | 7 | 7 |
| Citric acid | 0.2 | 0.2 | 0.2 | 0.2 | 0.2 | 0 | 0 |
| Diethanolamine pentaphosphonic acid | 0.3 | 0.3 | 0.3 | 0.3 | 0.3 | 0 | 0.3 |
| Ethanol | 12 | 12 | 12 | 12 | 12 | 12 | 12 |
| Silicone suds suppressor emulsion, brightener, perfume, opacifier, dye, antioxidant and water | BALANCE TO 100 | | | | | | |

(a) Coconut fatty acid having a ratio : lauric to myristic acid of 70 to 30.
(b) MAXATASE ® supplied by GIST-BROCADES expressed on 100% active enzyme-basis.
(c) Total calcium is expressed as millimoles of calcium per kilo of composition and added as calcium chloride.

Compositions VI–XII are clear, homogeneous products having a markedly improved enzyme stability, especially upon storage.

EXAMPLE XIII

In the following compositions, the general formula was as follows:

| Ingredient | % of Formula |
|---|---|
| Sodium $C_{12, 14, 16}$ alkyl polyethylene $oxide_3$ sulfate | 12.25 |
| $C_{12-13}$ alkyl polyethoxylate$_{6.5}$ | 22.8 |
| Ethanol | 10 |
| Sodium formate | As indicated below |
| Alkaline buffering agent | As indicated below |
| Calcium chloride | As indicated below |
| Maxazyme (Maxatase) enzyme solution (.032 Anson units/g. of product, contains 500 mg./liter $Ca^{++}$) | 1.6 |
| Water (contains $Ca^{++}$ and $Mg^{++}$) and minors | Balance |

The above general formula was modified by adding the indicated percentages of alkaline buffering agents (citric acid to trim) to provide the indicated product pH's and by adding the indicated percentages of $CaCl_2$ and sodium formate. The individual compositions were tested and gave the indicated stability results

|  | A | B | C | D | E |
|---|---|---|---|---|---|
| % monoethanolamine (MEA) | — | — | — | — | — |
| % triethanolamine (TEA) | — | 2.44 | 2.44 | 2.44 | 2.0 |
| % sodium formate | 1.0 | 6.0 | 3.0 | 1.0 | 1.0 |
| Added $CaCl_2$ | 0 | ←saturated→ | | | 0 |
| pH | 7.5 | 9.0 | 9.0 | 9.0 | 9.6 |
| % Retained enzyme activity after storage for one week at 120° F. | 91 | 78 | 71 | 67 | 46 |
|  | CONTROL | TEA EXAMPLES | | | |

|  | F | G | H | I | J |
|---|---|---|---|---|---|
| % monoethanolamine (MEA) | 1.0 | 1.0 | 1.0 | 1.0 | 1.0 |
| % triethanolamine (TEA) | — | — | — | — | — |
| % sodium formate | 6.0 | 3.0 | 1.0 | 3.0 | 1.0 |
| Added $CaCl_2$ | ←saturated→ | | | 0 | 0 |
| pH | 9.0 | 9.0 | 9.0 | 9.0 | 9.0 |
| % Retained enzyme activity after storage for one week at 120° F. | 57 | 52 | 43 | 41 | 17 |
|  | MEA EXAMPLES | | | | |

|  | K | L | M | N | O | P |
|---|---|---|---|---|---|---|
| % monoethanolamine | — | — | — | — | — | — |
| % triethanol amine | 1.22 | 1.22 | 1.22 | — | — | — |
| % $Na_2CO_3$ | 0.87 | 0.87 | 0.87 | 1.0 | 1.0 | 1.0 |
| % sodium formate | 6.0 | 3.0 | 1.0 | 1.0 | 1.0 | 1.0 |
| Added $CaCl_2$ | ←saturated→ | | | — | — | — |
| pH | 9.0 | 9.0 | 9.0 | 8.0 | 9.0 | 10.0 |
| % Retained enzyme activity after storage for one week at 120° F. | 5 | 13 | 0 | 38 | 35 | 5 |
|  | Effect of carbonate + TEA | | | pH effect with carbonate | | |

The stability of each individual composition was compared to that of the control sample A, which is at low pH and contains no added buffering agent. Samples containing TEA (B,C,D) are more stable than their MEA counterparts (F,G,H), which in turn are much superior to formulas containing $Na_2CO_3$ (K-P). Enzyme degradation is retarded with increasing levels of sodium formate, particularly in ethanolamine-buffered systems (compare B to F, C to G, and D to H). Added $Ca^{++}$ (in the form of $CaCl_2$) to the point of saturation retards the degradation rate (compare G to I and H to J).

What is claimed is:

1. A stabilized aqueous enzyme composition consisting essentially of:
   (a) from 0% to about 75% of a detergent surfactant selected from the group consisting of nonionic, anionic, cationic, zwitterionic, amphoteric and semi-polar nonionic surfactants and mixtures thereof;
   (b) from about 0.025% to about 10% pure proteolytic enzyme;
   (c) from 0 to about 60% of a low molecular weight primary or secondary alcohol;
   (d) from about 3% to about 10% of a water soluble formate;
   (e) a soluble calcium salt to give from about 2 to about 10 millimoles of calcium ion per liter;
   (f) triethanolamine as an alkaline buffering agent; and
   (g) the balance water,
the pH of the product being from about 8.5 to about 10.

2. The composition of claim 1 containing from about 5% to about 15% of said alcohol; from about 4% to about 8% of sodium formate; and from about 4 to about 8 millimoles of calcium ion per liter, the pH being from about 9 to about 9.5.

3. The composition of claim 2 wherein the alcohol is selected from the group consisting of methanol, ethanol, propanol, and isopropanol, and mixtures thereof.

4. The composition of claim 3 wherein the surfactant is present in an amount of from about 20% to about 50%.

5. The composition of claim 3 wherein the detergent surfactant is a mixture of anionic and nonionic surfactants.

6. The composition of claim 3 wherein the detergent surfactant is a mixture of nonionic and cationic surfactants.

7. The composition of claim 3 wherein the detergent surfactant is a mixture of nonionic and semi-polar nonionic surfactants.

8. The composition of claim 3 wherein the alcohol is ethyl alcohol.

9. The composition of claim 3 wherein the proteolytic enzyme is present at a level of from about 0.05% to about 0.2% to give a level of enzyme activity of from about 15 to about 60 Anson units per liter, and wherein the enzyme has an isoelectric point of at least about 8.5.

10. The composition of claim 3 which is substantially free of carbonate ions.

* * * * *